US011337868B2

(12) United States Patent
Fukasawa et al.

(10) Patent No.: US 11,337,868 B2
(45) Date of Patent: May 24, 2022

(54) PULL-ON ABSORBENT ARTICLE INCLUDING LEG-CIRCUMFERENCE EXTENSION SECTIONS WITH WELDED REGIONS

(71) Applicant: UNICHARM CORPORATION, Shikokuchuo (JP)

(72) Inventors: Jun Fukasawa, Kagawa (JP); Toshiyasu Yoshioka, Kagawa (JP); Kunihiko Katsuragawa, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 516 days.

(21) Appl. No.: 16/326,710

(22) PCT Filed: Jul. 5, 2017

(86) PCT No.: PCT/JP2017/024694
§ 371 (c)(1),
(2) Date: Feb. 20, 2019

(87) PCT Pub. No.: WO2018/042874
PCT Pub. Date: Mar. 8, 2018

(65) Prior Publication Data
US 2019/0192357 A1 Jun. 27, 2019

(30) Foreign Application Priority Data
Aug. 29, 2016 (JP) .............................. JP2016-167105

(51) Int. Cl.
*A61F 13/496* (2006.01)
*A61F 13/49* (2006.01)
(Continued)

(52) U.S. Cl.
CPC .......... *A61F 13/4963* (2013.01); *A61F 13/49* (2013.01); *A61F 13/494* (2013.01);
(Continued)

(58) Field of Classification Search
CPC ............ A61F 13/49406; A61F 13/4963; A61F 13/49; A61F 13/494; A61F 2013/15861
See application file for complete search history.

(56) References Cited

U.S. PATENT DOCUMENTS 6,123,694 A * 9/2000 Pieniak ............... A61F 13/4942
604/385.01
8,043,275 B2 * 10/2011 Peterson ............. A61F 13/4942
604/385.28
(Continued)

FOREIGN PATENT DOCUMENTS

EP 3318229 A1 5/2018
JP 2002522117 A 7/2002
(Continued)

OTHER PUBLICATIONS

Office Action in IN Application No. 201927003177, dated Jun. 22, 2021, 7pp.
(Continued)

*Primary Examiner* — Michele M Kidwell
(74) *Attorney, Agent, or Firm* — Hauptman Ham, LLP

(57) ABSTRACT

A pull-on absorbent article includes: an absorbent main body including an absorbent body along a vertical direction; and waist-circumference sections in a pair respectively located on one end side and another end side of the absorbent main body, the waist-circumference sections each including an elastic member stretchable in a lateral direction, the absorbent main body including extension sections in a pair respectively extending outward on two lateral sides of the absorbent body, the extension sections each having an elastic member stretchable in the vertical direction placed therein, the extension sections each forming a leg opening and including an overlap portion that overlaps in the vertical direction with at least one of the waist-circumference sections in a pair, the overlap portion having at least a part
(Continued)

joined to the waist-circumference section, the overlap portion of the extension section having a welded region having a predetermined lateral length placed therein.

6 Claims, 9 Drawing Sheets

(51) Int. Cl.
*A61F 13/494* (2006.01)
*A61F 13/15* (2006.01)

(52) U.S. Cl.
CPC ............... *A61F 13/49406* (2013.01); *A61F 2013/15861* (2013.01)

(56) References Cited

U.S. PATENT DOCUMENTS

| | | | | |
|---|---|---|---|---|
| 10,925,778 | B2* | 2/2021 | Mukai | A61F 13/4942 |
| 2003/0171731 | A1* | 9/2003 | Johnston | A61F 13/4942 |
| | | | | 604/385.27 |
| 2010/0100069 | A1* | 4/2010 | Nakaoka | A61F 13/4753 |
| | | | | 604/385.101 |
| 2012/0277703 | A1* | 11/2012 | Rhein | A61F 13/51104 |
| | | | | 604/369 |
| 2013/0255865 | A1* | 10/2013 | Brown | A61F 13/15593 |
| | | | | 156/161 |
| 2016/0278996 | A1* | 9/2016 | Takahashi | A61F 13/4942 |
| 2017/0239104 | A1* | 8/2017 | Jang | A61F 13/49011 |
| 2019/0254884 | A1* | 8/2019 | Mukai | A61F 5/44 |
| 2019/0254886 | A1* | 8/2019 | Kokturk | A61F 13/15804 |

FOREIGN PATENT DOCUMENTS

| | | |
|---|---|---|
| JP | 2005-80859 A | 3/2005 |
| JP | 2008-168012 A | 7/2008 |
| JP | 2009-160128 A | 7/2009 |
| JP | 2010-70743 A | 4/2010 |
| JP | 2010-194228 A | 9/2010 |
| WO | 00/07534 A1 | 2/2000 |
| WO | 2005/105010 A1 | 11/2005 |
| WO | 2011/040046 A1 | 4/2011 |
| WO | 2017002461 A1 | 1/2017 |

OTHER PUBLICATIONS

Office Action in JP Application No. 2016-167105, dated May 12, 2020, 2pp.
International Preliminary Report on Patentability in PCT Application No. PCT/JP2017/024694, dated Sep. 12, 2017, 11pp.
Office Action in CN Application No. 201790001190.6 dated Nov. 25, 2019, 1pp.
International Search Report in PCT Application No. PCT/JP2017/024694, dated Sep. 12, 2017, 4pp.
Extended European Search Report in EP Application No. 17845884.0, dated Jul. 12, 2019, 8pp.
Office Action in EA Application No. 201990600/31, dated May 28, 2020, 4pp.

* cited by examiner

PULL-ON ABSORBENT ARTICLE INCLUDING LEG-CIRCUMFERENCE EXTENSION SECTIONS WITH WELDED REGIONS

RELATED APPLICATIONS

The present application is a National Phase of PCT/JP2017/024694, filed Jul. 5, 2017, and claims priority based on Japanese Patent Application No. 2016-167105, filed Aug. 29, 2016.

TECHNICAL FIELD

The present disclosure relates to a pull-on absorbent article.

BACKGROUND ART

An example of an absorbent article includes a pull-on disposable diaper in which a front panel and a back panel are pre-joined at both side portions thereof. Patent Literature 1 discloses a disposable diaper in which an outer sheet configuring a front panel and a back panel are folded over at a waist section, with a waist stretchable member being placed between the outer sheet and the folded portion thereof as well as a cushion forming sheet being placed between the waist stretchable member and the folded portion. Further, in this diaper, the folded portion of the outer sheet and the cushion forming sheet are joined together discontinuously in a direction along the waist circumference. Accordingly, gaps are formed between the cushion forming sheet and non-joined portions of the folded portion, thereby being able to reduce irritation caused to the wearer's skin. In order to prevent lateral leakage of excrement, this diaper is also provided with integrated barrier cuffs that are respectively raised based on the two side edges of an absorbent body. The barrier cuffs extend from the crotch portion to the front panel and the back panel, and intersect the waist stretchable member.

CITATION LIST

Patent Literature

[PTL 1] Japanese Patent Application Publication No. 2010-70743

SUMMARY OF INVENTION

Technical Problem

Further, known is an absorbent article that includes, in addition to barrier cuffs described above, a pair of extension sections (so-called leg gathers) that respectively extend laterally outward of an absorbent body to form leg openings and have elastic members stretchable in a vertical direction disposed therein. By closely fitting the extension sections around the wearer's legs, lateral leakage of excrement can be further prevented. In a case in which the extension sections extend from the crotch portion to the front panel and the back panel, similarly to the barrier cuffs described above, and are joined thereto, the extension sections are likely to be affected by the waist stretchable member, and might contract or curl in the lateral direction. This cannot closely fit the extension sections around the wearer's legs, thereby being able to reduce their effectiveness in preventing lateral leakage.

The present disclosure has been achieved in consideration of such issues as describe above, an object of the present disclosure is to provide a pull-on absorbent article that is suppressed from leaking from around the legs.

Solution to Problem

A primary aspect of the present disclosure is a pull-on absorbent article having a vertical direction and a lateral direction, the pull-on absorbent article comprising: an absorbent main body including an absorbent body, the absorbent main body having a longitudinal direction that conforms to the vertical direction; and waist-circumference sections in a pair respectively located on one end side and another end side in the longitudinal direction of the absorbent main body, the waist-circumference sections including an elastic member stretchable in the lateral direction, the absorbent main body including extension sections in a pair respectively extending outward on two lateral sides of the absorbent body, the extension sections each having an elastic member stretchable in the vertical direction placed therein, the extension sections each forming a leg opening and including an overlap portion that overlaps in the vertical direction with at least one of the waist-circumference sections in a pair, the extension section and the waist-circumference section being joined together in at least a part of the overlap portion, the overlap portion, in the extension section, having a welded region placed therein, the welded region having a predetermined length in the lateral direction.

At least following matter will become clear from the descriptions of the present specification with reference to the accompanying drawings.

Advantageous Effects of Invention

According to the present disclosure, it is possible to provide a pull-on absorbent article that is suppressed from leaking from around legs.

DESCRIPTION OF EMBODIMENTS

Figure 1:
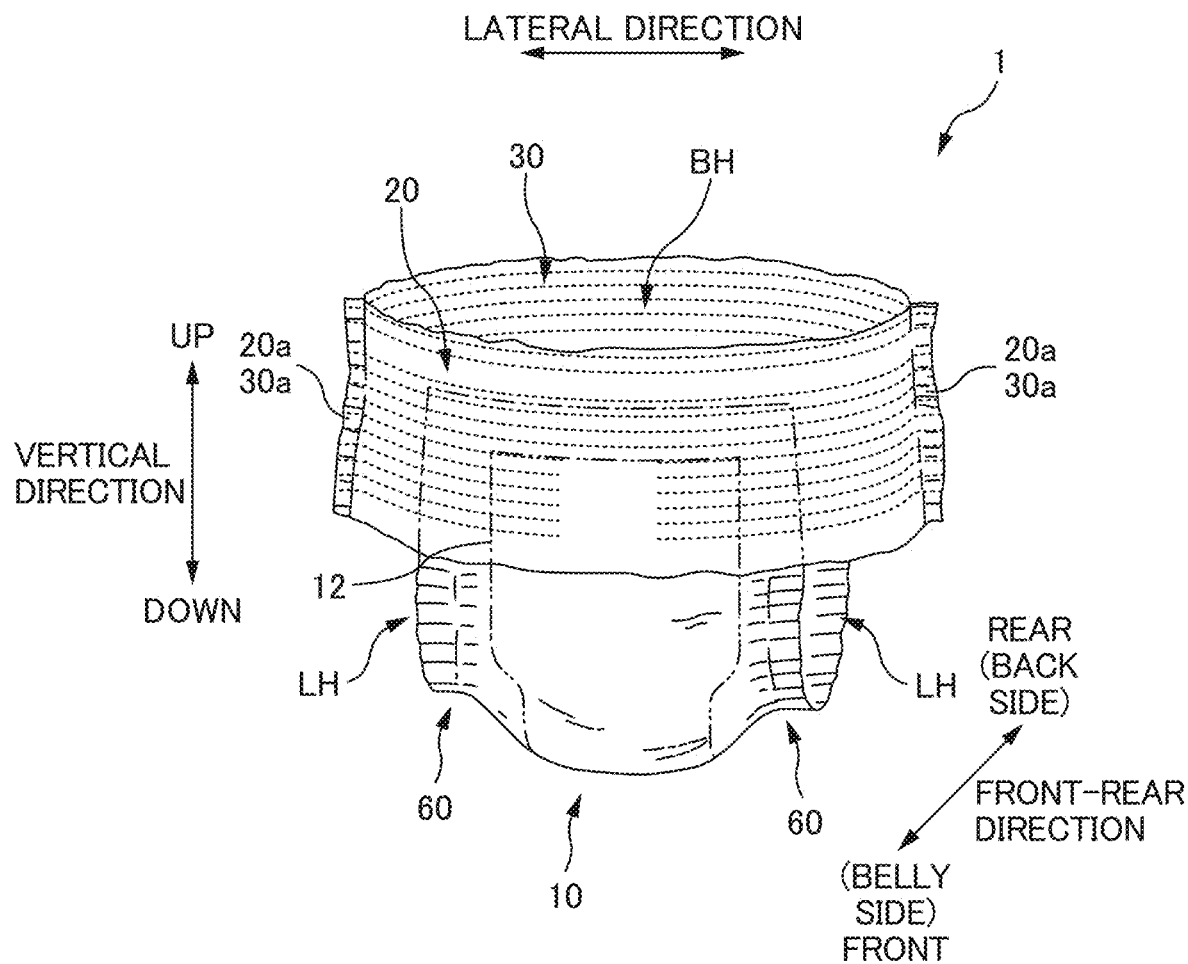
FIG. 1 is a schematic perspective view of a pull-on disposable diaper 1.

At least following matters will become clear from the descriptions of the present specification with reference to the accompanying drawings.

A pull-on absorbent article having a vertical direction and a lateral direction, the pull-on absorbent article comprising: an absorbent main body including an absorbent body, the absorbent main body having a longitudinal direction that conforms to the vertical direction; and waist-circumference sections in a pair respectively located on one end side and another end side in the longitudinal direction of the absorbent main body, the waist-circumference sections including an elastic member stretchable in the lateral direction, the absorbent main body including extension sections in a pair respectively extending outward on two lateral sides of the absorbent body, the extension sections each having an elastic member stretchable in the vertical direction placed therein, the extension sections each forming a leg opening and including an overlap portion that overlaps in the vertical direction with at least one of the waist-circumference sections in a pair, the extension section and the waist-circumference section being joined together in at least a part of the overlap portion, the overlap portion, in the extension section, having a welded region placed therein, the welded region having a predetermined length in the lateral direction.

According to such a pull-on absorbent article, lateral stiffness of the overlap portion is enhanced by virtue of the welded region, thereby being able to suppress the overlap portion from contracting in the lateral direction. Accordingly, the extension sections are likely to be maintained wide in lateral width. This closely fits the extension sections around the legs of the wearer through face contact, thereby suppressing leakage from around the legs.

Such a pull-on absorbent article is characterized in that a plurality of the elastic members stretchable in the lateral direction are placed at an interval in the vertical direction in the waist-circumference section, a plurality of the welded regions are placed at an interval in the vertical direction in the overlap portion of each of the extension sections, and the interval in the vertical direction between the plurality of elastic members placed in the waist-circumference section is smaller than the interval in the vertical direction between the plurality of welded regions.

According to such a pull-on absorbent article, it is possible to ensure the fit to a wearer in the waist-circumference sections, while suppressing lateral contraction of the overlap portions by virtue of the welded regions, thereby suppressing leakage from around the legs.

Such a pull-on absorbent article is characterized in that the overlap portion includes a non-joined region at a position corresponding to a lower end portion in the vertical direction of the waist-circumference section, the non-joined region being a region where the extension section and the waist-circumference section are not joined together, and the welded region is placed in the non-joined region.

According to such a pull-on absorbent article, the non-joined region, which is the boundary portion between the overlap portion and a portion other than the overlap portion in the extension section is not likely to contract in the lateral direction. Accordingly, the portion other than the overlap portion in the extension section, that is, the portion forming the leg opening, is likely to be maintained wide in lateral width, and is able to closely fit around each leg of the wearer, thereby suppressing leakage from around the legs more reliably.

Such a pull-on absorbent article is characterized in that the welded region and the elastic member that is placed in the waist-circumference section are not superimposed on each other in plan view in a thickness direction of the extension section.

According to such a pull-on absorbent article, it is possible to prevent a portion overlapping with the overlap portion of the elastic member from being excessively suppressed from being contracted by the welded region, the overlap portion being placed in the waist-circumference section, thereby being able to ensure the fit to the wearer in the waist-circumference section.

Such a pull-on absorbent article is characterized in that the welded region includes a first welded region and a second welded region, the second welded region being positioned on a non-skin side in the thickness direction of the extension section with respect to the first welded region.

According to such a pull-on absorbent article, the lateral stiffness of the overlap portions is further increased, thereby further suppressing the overlap portion from contracting in the lateral direction. Accordingly, the extension sections are likely to be maintained wide in lateral width, thereby suppressing leakage from around the legs more reliably.

Such a pull-on absorbent article is characterized in that at least a portion of the first welded regions and at least a portion of the second welded regions are not superimposed on each other in plan view in the thickness direction.

According to such a pull-on absorbent article, the welded regions are present over a wider range in a flat plane in the overlap portion, the stiffness is increased over a wider range in a flat plane in the overlap portions, thereby suppressing lateral contraction of the overlap portion. Accordingly, the extension sections are likely to be maintained wide in lateral width, thereby suppressing leakage from around the legs more reliably.

Such a pull-on absorbent article is characterized in that the elastic member placed in the waist-circumference section includes a discontinuous portion in a portion superimposed on the absorbent body in a thickness direction of the waist-circumference section.

According to such a pull-on absorbent article, the absorbent body is not likely to be affected by contraction of the elastic member placed in the waist-circumference section, thereby suppressing twisting of the absorbent body. Accordingly, the absorbent body can closely fit the wearer so that excrement is reliably absorbed, thereby suppressing leakage from around the legs.

Embodiments

A pull-on absorbent article according to the present disclosure will now be described using the following embodiment in which a "pull-on disposable diaper" is employed as an example thereof. The pull-on disposable diaper according to an embodiment of the present disclosure may be used for infants or adults. The pull-on absorbent article according to the present disclosure may also be used in applications other than disposable diapers, such as a shorts style sanitary napkin, for example.

Basic Configuration of Pull-On Disposable Diaper

Figure 2:
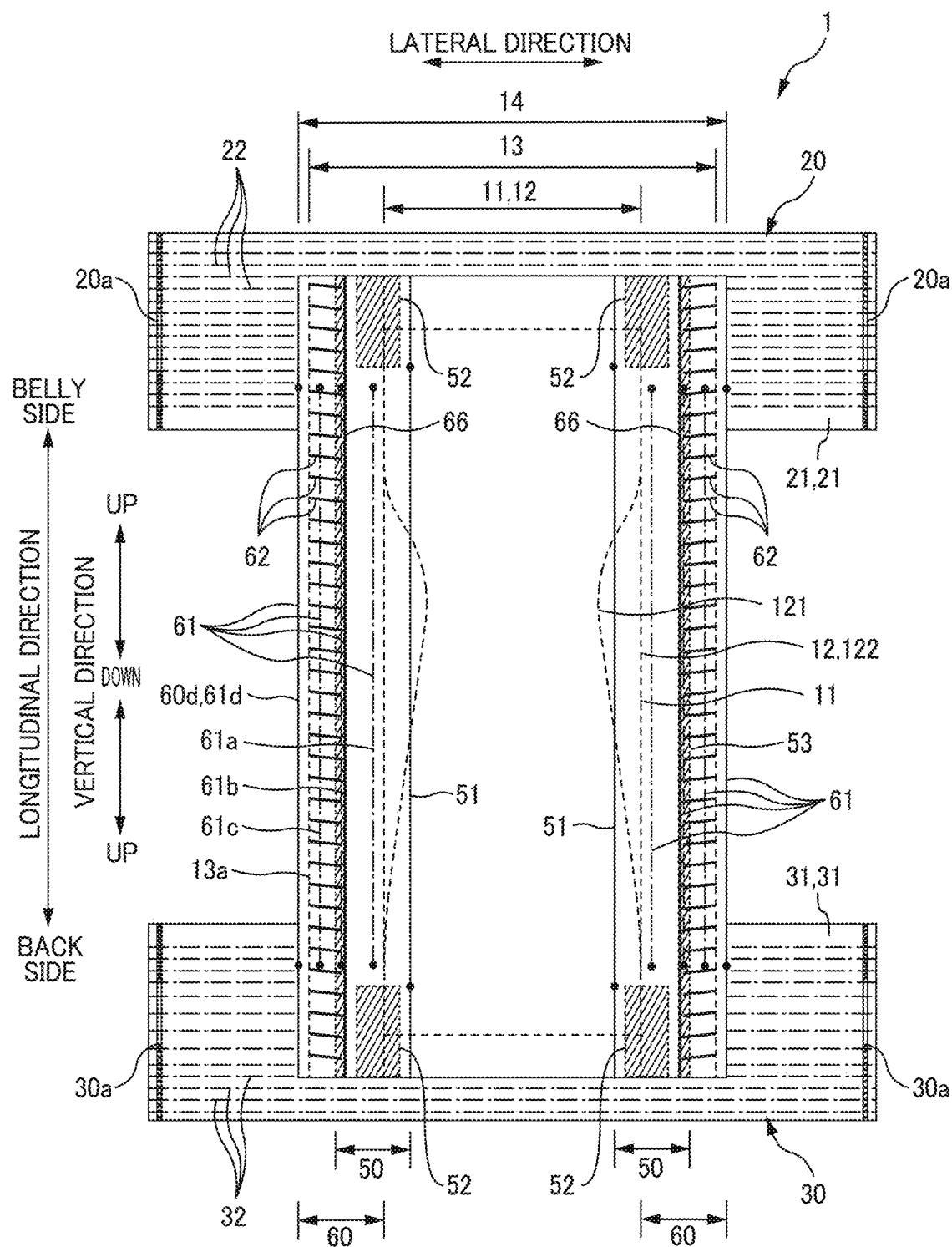
FIG. 2 is a schematic plan view of the diaper 1 in an unfolded and extended state when viewed from a skin-side.
Figure 3:
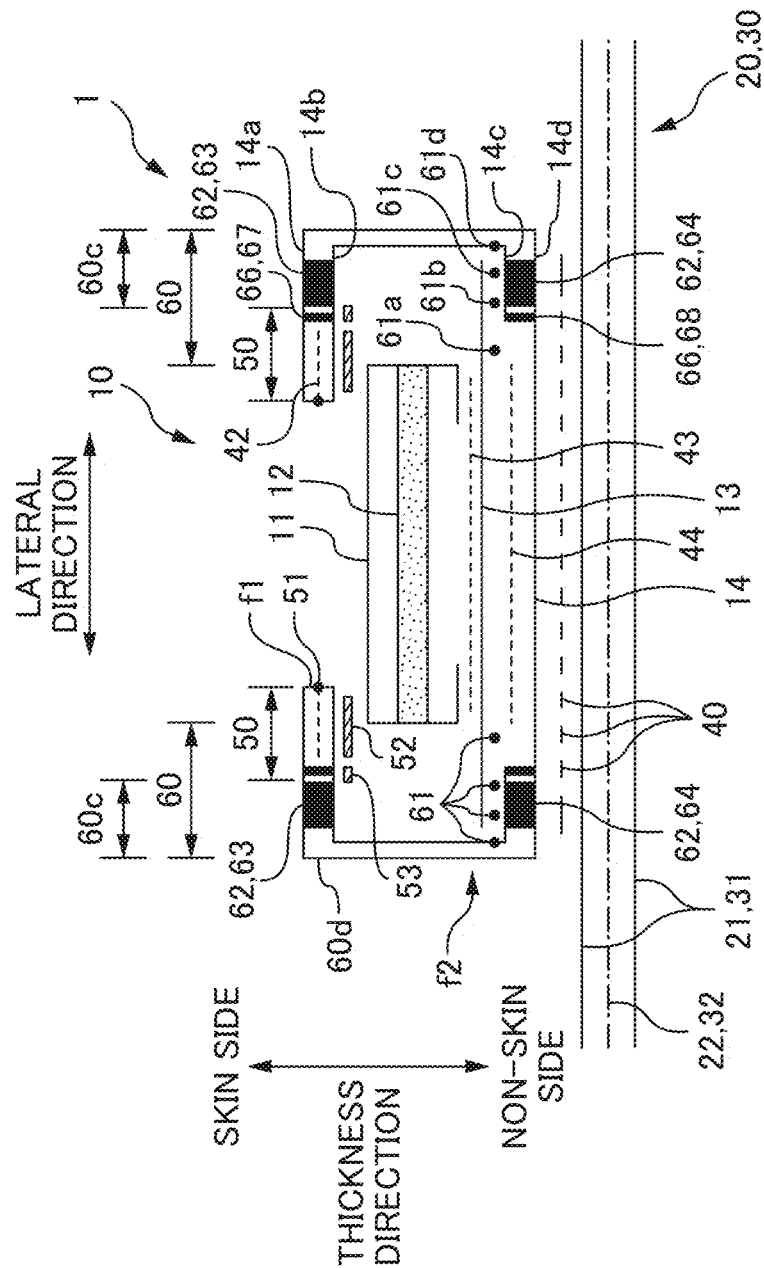
FIG. 3 is a schematic cross-section of the diaper 1.
Figure 4A:
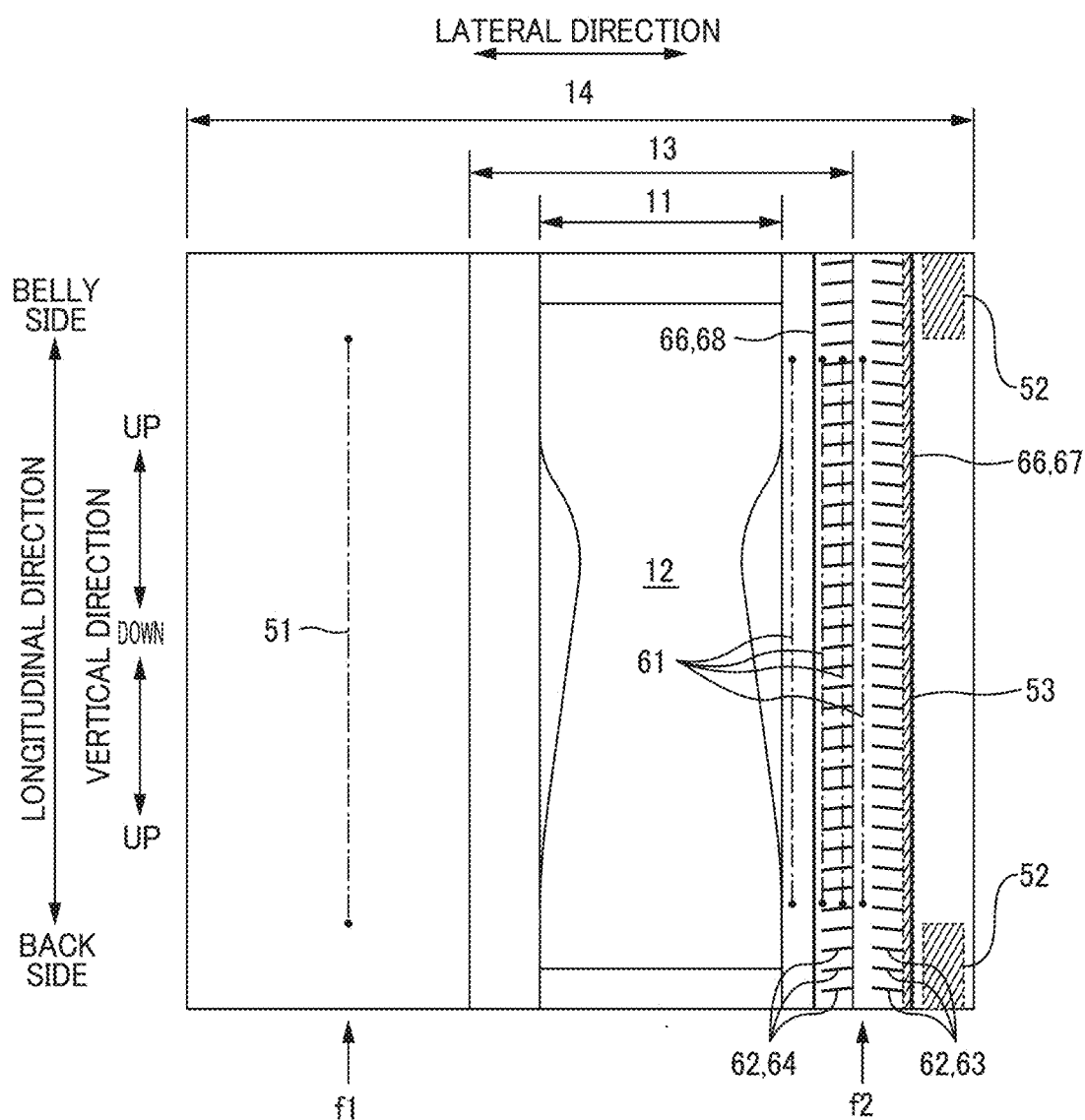
FIG. 4A and FIG. 4B are diagrams to explain a method of forming an absorbent main body 10.
Figure 4B:
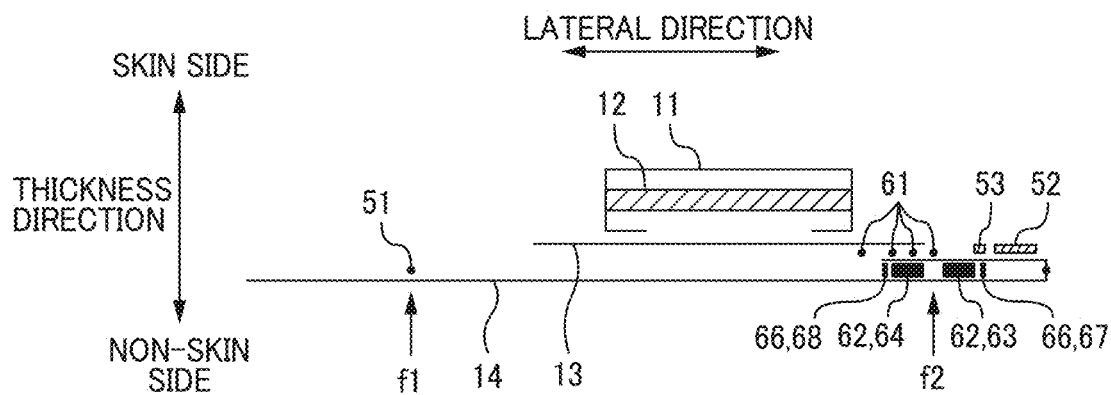
Figure 5:
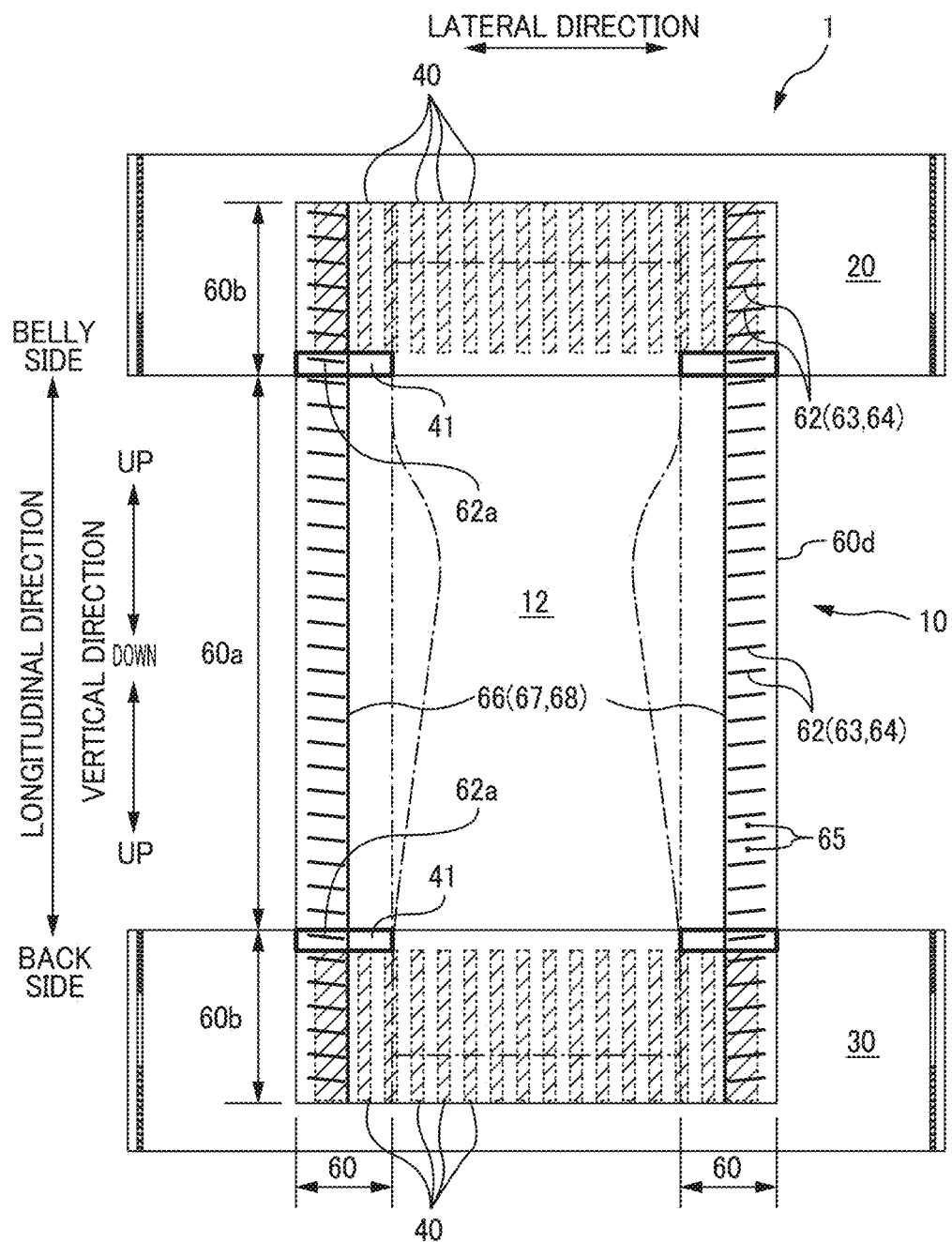
FIG. 5 is an explanatory diagram of the absorbent main body 10 and adhesive regions 40 of a pair of waist-circumference sections 20, 30.

FIG. 1 is a schematic perspective view of a pull-on disposable diaper 1 (hereinafter referred to as a "diaper"). FIG. 2 is a schematic plan view of the diaper 1 in an unfolded and stretched state, as viewed from a skin-side face. FIG. 3 is a schematic cross-section of the diaper 1. FIG. 4A and FIG. 4B are diagrams to explain a method of forming an absorbent main body 10. FIG. 5 is an explanatory diagram of the absorbent main body 10 and adhesive regions 40 of a pair of waist-circumference sections 20, 30. Note that, except for FIG. 1, the drawings illustrate states in which the diaper 1 provided with elastic members has been stretched to such an extent that creases in the diaper 1 are not visible. Specifically, the stretched state illustrated indicates a state of having been stretched such that the dimensions of members configuring the diaper 1 (such as an exterior sheet 14 described later, for example) match or are close to the dimensions of the individual members of their own.

As illustrated in FIG. 1, a vertical direction, a lateral direction, and a front-rear direction are defined in the pull-on diaper 1. A waist opening BH and a pair of leg openings LH are formed in the diaper 1. In the vertical direction, the side of the waist opening BH is an upper side, and the side that will be disposed at the crotch of a wearer is a lower side. In the front-rear direction, the side that will be disposed on the wearer's belly side is a front side, and the side that will be disposed on the wearer's back side is a rear side. The diaper 1 has a thickness direction as illustrated in FIG. 3. The side in the thickness direction that will contact the wearer is a skin side, and the opposite side thereto is the non-skin side.

The diaper 1 is what is referred to as a three-piece type of diaper, and includes an absorbent main body 10 and a pair of waist-circumference sections 20, 30. The absorbent main body 10 has a substantially rectangular shape in plan view, with the longitudinal direction thereof oriented along the vertical direction. The waist-circumference sections 20, 30 have substantially rectangular shapes in plan view, with the longitudinal directions thereof oriented along the lateral direction. The waist-circumference section that will cover a belly part of the wearer out of the pair of waist-circumference sections 20, 30 is also referred to as a front waist-circumference section 20, and the waist-circumference section that will cover a back part of the wearer is also referred to as a back waist-circumference section 30.

As illustrated in the unfolded state in FIG. 2, a central portion of the front waist-circumference section 20 in the lateral direction is positioned on one longitudinal end side of the absorbent main body 10, and a central portion of the back waist-circumference section 30 in the lateral direction is positioned on the other longitudinal end side of the absorbent main body 10. The non-skin-side face of the absorbent main body 10 and the skin-side faces of the pair of waist-circumference sections 20, 30 are then joined together with an adhesive agent or the like at the adhesive regions 40 illustrated in FIG. 5. From the unfolded state of FIG. 2, the absorbent main body 10 is folded in two by folding the absorbent main body 10 at its substantially central portion in the longitudinal direction such that the front waist-circumference section 20 and the back waist-circumference section 30 are superimposed on each other. Then, by joining two lateral side portions 20a of the front waist-circumference section 20 to two lateral side portions 30a of the back waist-circumference section 30, respectively, the diaper 1 is formed into a pull-on diaper.

The front waist-circumference section 20 and the back waist-circumference section 30 each include two soft sheets (21 and 21, and 31 and 31) of a nonwoven fabric or the like, and a plurality of elastic members 22, 32 such as laterally stretchable elastic strings or the like. In the following description, the elastic members 22, 32 are also referred to as waist-circumference elastic members 22, 32. The plural waist-circumference elastic members 22, 32 are arranged in rows and spaced apart from each other in the vertical direction, and are fixed between the two sheets (21 and 21 or 31 and 31) in a stretched state along the lateral direction. The front waist-circumference section 20 and the back waist-circumference section 30 are accordingly stretchable in the lateral direction, so as to fit the waist of the wearer.

The absorbent main body 10 includes a top sheet 11, an absorbent body 12, a back sheet 13, and the exterior sheet 14, in this order in the thickness direction from the skin side, as illustrated in FIG. 3. The top sheet 11 may be any sheet as long as it is a liquid permeable sheet, and examples thereof include a hydrophilic air-through nonwoven fabric and a hydrophilic spunbond nonwoven fabric. The back sheet 13 may be any sheet as long as it is a liquid impermeable sheet, and examples thereof include a polyethylene film, a polypropylene film, and the like. The top sheet 11 and the back sheet 13 have sizes that covers the entire absorbent body 12. In an embodiment of the present disclosure, the side portions on the two lateral sides of the top sheet 11 are folded to the non-skin side of the absorbent body 12. The exterior sheet 14 may be a liquid permeable sheet or a liquid impermeable sheet. However, in an embodiment of the present disclosure, since the leak prevention wall sections 50 are formed using the exterior sheet 14, examples of the exterior sheet 14 include a hydrophobic SMS nonwoven fabric and the like.

The absorbent body 12 has a substantially rectangular shape in plan view, and includes an absorbent core 121 for absorbing liquid, and a core-wrapping sheet 122 covering outer peripheral faces of the absorbent core 121. The absorbent core 121 is configured such that a liquid-absorbent material is molded into a predetermined shape and, in an embodiment of the present disclosure, is molded into a substantially hour-glass shape having a narrowed central portion in the longitudinal direction thereof. Examples of the liquid-absorbent material include materials obtained by containing a highly absorbent polymer (so-called a SAP) in liquid-absorbent fibers, such as pulp fibers. Examples of the core-wrapping sheet 122 include a liquid permeable sheet such as tissue paper, a nonwoven fabric, or the like. Note that the core-wrapping sheet 122 need not be provided.

The absorbent main body 10 includes the pair of leak prevention wall sections 50 and a pair of leg-circumference extension sections 60 (a pair of extension sections). More details are described later, however, in an embodiment of the present disclosure, the pair of leak prevention wall sections 50 and the pair of leg-circumference extension sections 60 are integrally formed such that the two lateral side portions of the single exterior sheet 14 are folded, as illustrated in FIG. 3 and FIG. 4.

The leak prevention wall sections 50 in a pair extend along the longitudinal direction of the absorbent main body 10, and are provided at the two lateral side portions of the absorbent body 12, respectively. More specifically, the leak prevention wall sections 50 are provided so as to span from a position superimposed on the absorbent body 12 to a position extended laterally outward therefrom. The leak prevention wall sections 50 each includes: an elastic member 51 stretchable in the longitudinal direction (the vertical direction of the diaper 1); and a pair of end joined portions 52 and a side joined portion 53 where the exterior sheet 14 for forming the leak prevention wall sections 50 is joined to the top sheet 11 and the back sheet 13. The pairs of end joined portions 52 are respectively placed at the two longitudinal end portions of the absorbent main body 10. The side joined portions 53 in a pair extend from one end to the other end in the longitudinal direction of the absorbent main body 10, and are placed outside in the lateral direction of the end joined portions 52. Thus, in each of the leak prevention wall sections 50, a portion in the exterior sheet 14 between the pair of end joined portions 52 is raisable toward the wearer (the skin side in the thickness direction) based on the side joined portion 53 by virtue of contraction of the elastic members 51. Accordingly, excrement having laterally flown out is blocked by the leak prevention wall sections 50. However, the diaper 1 may also be configured without the leak prevention wall sections 50.

The leg-circumference extension sections 60 in a pair respectively are parts that extend outwards to the two lateral sides of the absorbent body 12. More specifically, the leg-circumference extension sections 60 are defined as parts from the respective laterally outer ends of the absorbent body 12 to the laterally outer ends of the absorbent main body 10. Moreover, as illustrated in FIG. 5, the leg-circumference extension sections 60 each includes a "leg opening forming portion 60a" to form each of the leg openings LH, and a pair of "overlap portions 60b" that respectively overlap with the front waist-circumference section 20 and the back waist-circumference section 30 in the vertical direction. In other words, the leg-circumference extension sections 60 each include a pair of "overlap portions 60b" respectively superimposed on the front waist-circumference section 20 and the back waist-circumference section 30 in the thickness direction. Each of the leg-circumference extension sections 60 includes four elastic members 61 (hereinafter also referred to as leg-circumference elastic members 61) stretchable in longitudinal direction (the vertical direction of the diaper 1) and placed at intervals in the lateral direction. Accordingly, the leg opening forming portions 60a of the leg-circumference extension sections 60 fit around the legs of the wearer.

A plurality of "lateral welded regions 62 (welded regions of the present disclosure)" are placed in each of the leg-circumference extension sections 60 such that each lateral welded region extends along the lateral direction while being inclined with respect to the lateral direction. The plurality of lateral welded regions 62 include, as illustrated in FIG. 3, a plurality of first lateral welded regions 63 positioned on the skin side in the thickness direction, and a plurality of second lateral welded regions 64 positioned on the non-skin side in the thickness direction. The plurality of first lateral welded regions 63 and the plurality of second lateral welded regions 64 each are, as illustrated in FIG. 5, arranged at intervals in the longitudinal direction in a row over the entire longitudinal region of each of the leg-circumference extension sections 60.

"Vertical welded regions 66" extending along the vertical direction (longitudinal direction) are respectively placed in the leg-circumference extension sections 60 at positions laterally inside of the lateral welded regions 62. The vertical welded regions 66 are also placed over the entire longitudinal region of the leg-circumference extension sections 60, and include first vertical welded regions 67 positioned on the skin side in the thickness direction, and second vertical welded regions 68 positioned on the non-skin side in the thickness direction.

Although an example has been given in which string-shaped elastic members such as elastic strings are employed as the elastic members (22, 32, 51, 61) provided in the front waist-circumference section 20, the back waist-circumference section 30, the leak prevention wall sections 50, and the leg-circumference extension sections 60, it is not limited thereto. For example, a single or a plurality of sheet-shaped elastic members such as a stretchable film, a stretchable nonwoven fabric, or the like may be placed therein instead of elastic strings. Moreover, only the parts where stretchability is exhibited in the elastic members (so-called effective length parts) are illustrated in the drawings. Accordingly, parts of the elastic members where stretchability is not exhibited may exist on their longitudinally outer sides of the illustrated elastic members. The arrangement and numbers of the elastic members are not limited to those of the illustrated configuration.

Method of Forming the Absorbent Main Body 10

A simple description will now be given of a method of forming the pair of leak prevention wall sections 50 and the pair of leg-circumference extension sections 60 using the single exterior sheet 14, with reference to FIG. 4.

First, as illustrated on the left side of FIG. 4A and FIG. 4B, the elastic member 51 used for the leak prevention wall section 50 is fixed to each lateral side portion of the exterior sheet 14 in a stretched state along the longitudinal direction. Then, using the lateral position at which the elastic member 51 for each leak prevention wall section 50 is fixed as a fold position f1, the two lateral side portions of the exterior sheet 14 are folded over toward the skin side in the thickness direction (inwards in the lateral direction).

Then, as illustrated on the right side of FIG. 4A and FIG. 4B, the lateral welded regions 62 and the vertical welded regions 66 are formed by partially welding together portions in the exterior sheet 14 having been folded on itself to form a double layer. Specifically, in each of the portions where the exterior sheet 14 is a double layer, the plurality of first lateral welded regions 63 are formed in a portion on the laterally outer side and placed at intervals in the longitudinal direction, and the plurality of second lateral welded regions 64 are formed in a portion on the laterally inner side and placed at intervals in the longitudinal direction. The first vertical welded region 67 is formed laterally outside of the first lateral welded regions 63, and the second vertical welded region 68 is formed laterally inside of the second lateral welded regions 64. The welded regions 62, 66 may be formed by a known welding method, and examples thereof include heat sealing, ultrasonic welding, welding by laser irradiation, and the like.

An adhesive agent is then applied to the skin-side face of the double-layered exterior sheet 14 in a portion laterally outside of the lateral welded regions 62, so as to form the end joined portions 52 and the side joined portion 53 of the leak prevention wall sections 50. Then, the four leg-circumference elastic members 61 are fixed to the skin-side face of the exterior sheet 14 at a portion laterally inside of the side joined portion 53 in a stretched state along the longitudinal direction. Thereafter, the back sheet 13 and the absorbent body 12 wrapped in the top sheet 11 are superimposed on and joined to a central portion in the lateral direction of the exterior sheet 14.

Finally, the side portions at the two lateral sides of the exterior sheet 14 are respectively folded back onto the skin side in the thickness direction with respect to the top sheet 11 at respective fold positions f2 between the first lateral welded regions 63 and the second lateral welded regions 64, thereby forming the absorbent main body 10 illustrated in FIG. 3. That is, the side portions on the two lateral sides of the exterior sheet 14 each are folded to form a quadruple layer. This results in the first lateral welded regions 63 and the second lateral welded regions 64 being superimposed on each other in the thickness direction and the first vertical welded regions 67 and the second vertical welded regions 68 being superimposed on each other in the thickness direction. In the following description, respective portions of the exterior sheet 14 of a quadruple layer are also referred to as a first sheet portion 14a, a second sheet portion 14b, a third sheet portion 14c, and a fourth sheet portion 14d, in this order from the skin side in the thickness direction. Each leak prevention wall section 50 is constituted by the first sheet portion 14a and second sheet portion 14b, and each leg-circumference extension section 60 is constituted by the first sheet portion 14a to fourth sheet portion 14d.

Leg-Circumference Extension Section 60

Figure 6:
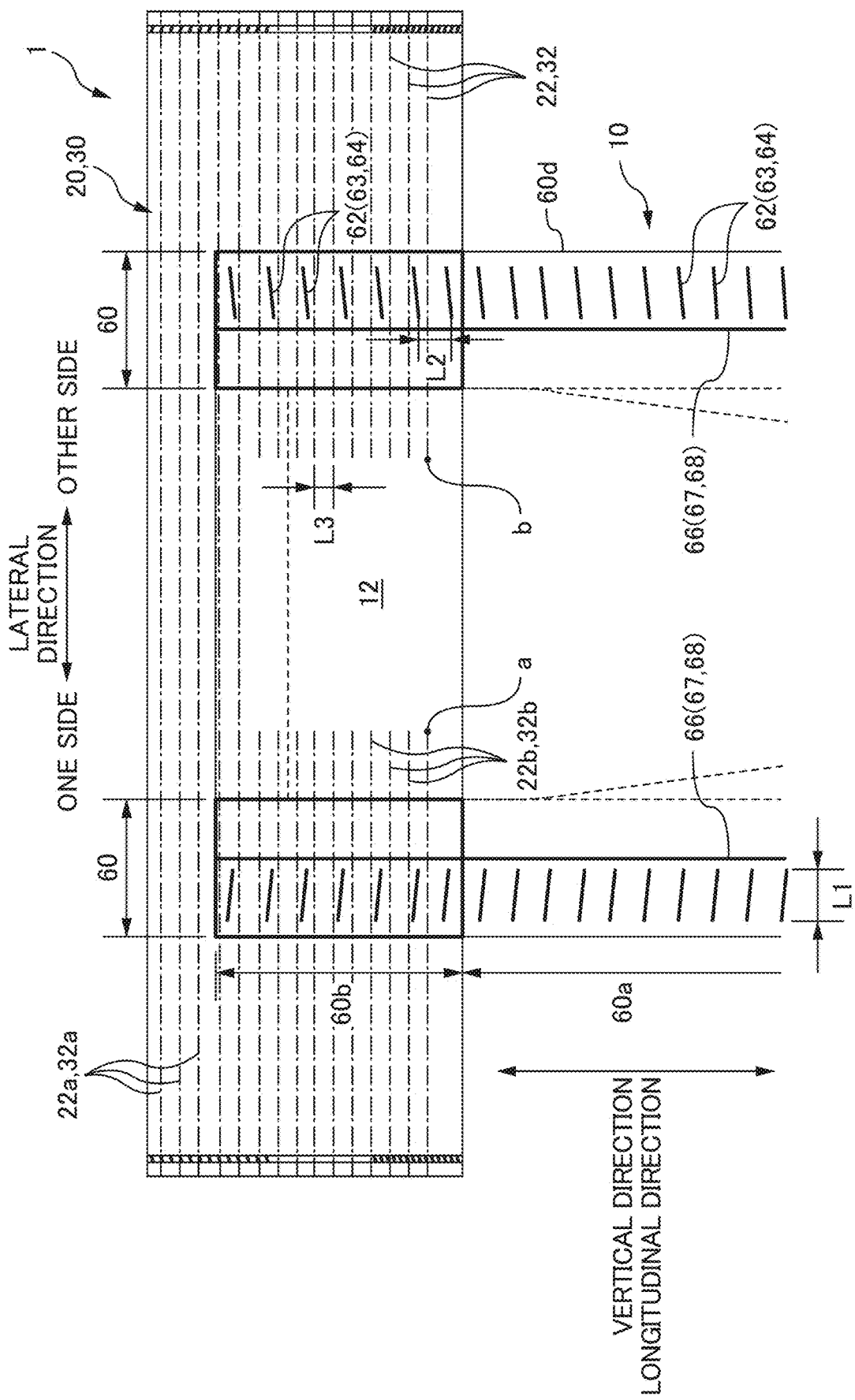
FIG. 6 is a diagram to explain characteristics of leg-circumference extension sections 60.
Figure 7:
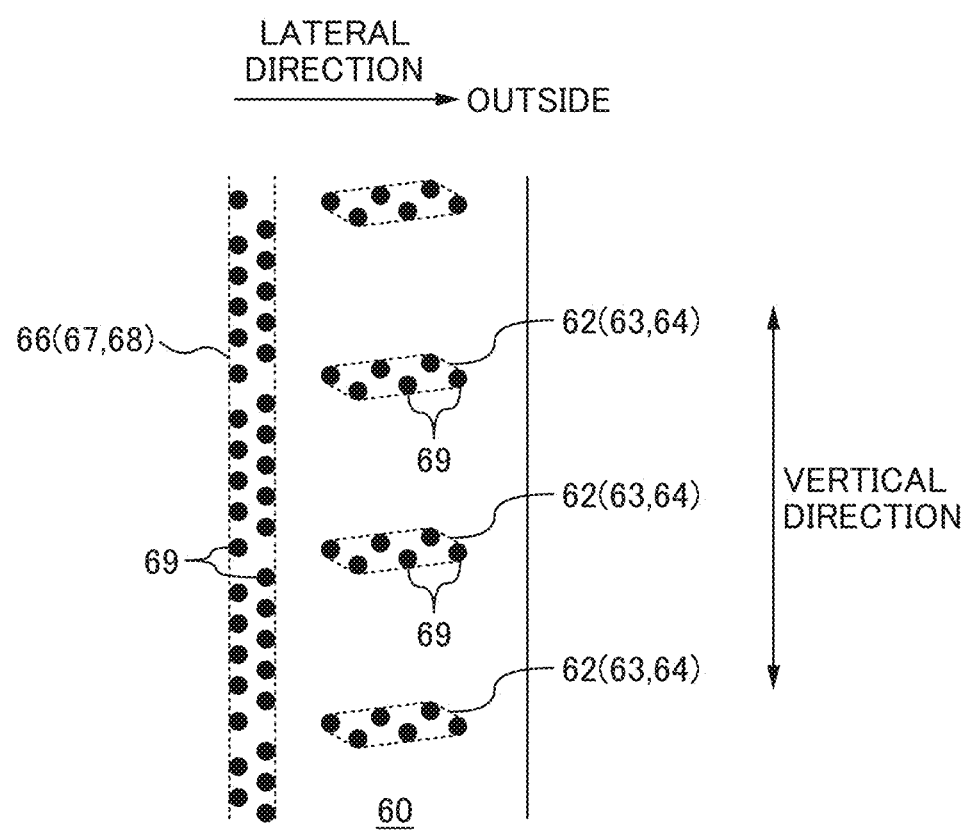
FIG. 7 is an enlarged diagram illustrating lateral welded regions 62 and vertical welded regions 66.
Figure 8:
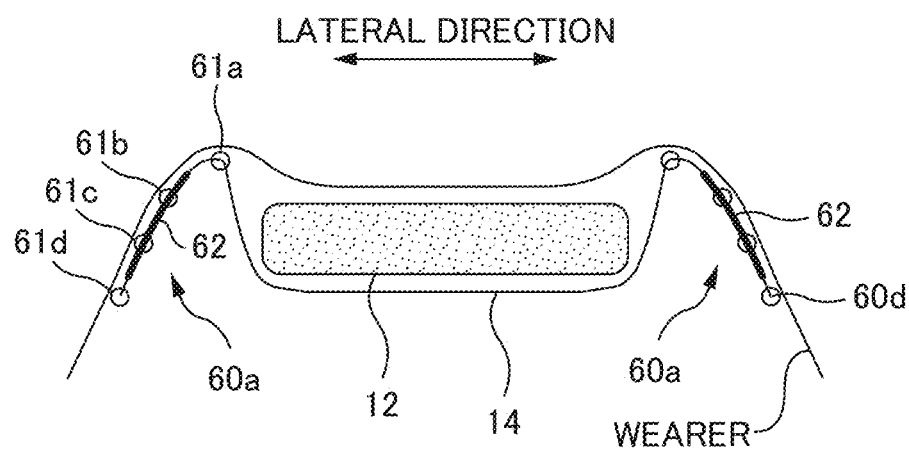
FIG. 8 is a diagram illustrating a state in which the leg-circumference extension sections 60 closely fit the wearer.

FIG. 6 is a diagram for explaining characteristics of the leg-circumference extension sections 60. FIG. 7 is an enlarged diagram illustrating the lateral welded regions 62 and the vertical welded regions 66. FIG. 8 is a diagram illustrating a state in which the leg-circumference extension sections 60 closely fit a wearer. Note that the leak prevention wall sections 50 and the like are omitted in FIG. 8 for the sake of brevity.

In the diaper 1 according to an embodiment of the present disclosure, the lateral width of the leg-circumference extension sections 60 is set to be comparatively wide. For example, in an S size infant diaper 1, when the lateral width of the absorbent main body 10 is 200 mm, the lateral width of each of the leg-circumference extension sections 60 is set at about 40 mm. This can closely fit the leg-circumference extension sections 60 around the legs of the wearer through a face having a wide width. Accordingly, excrement is not likely to leak from around the legs. Moreover, since the leg-circumference extension sections 60 are set at the wide lateral width, a plurality of strings (four in this case) of the leg-circumference elastic members 61 can be placed side by side at intervals in the lateral direction. Accordingly, the stretching force of the leg-circumference extension sections 60 that is necessary to stop lateral leakage can be shared among the plurality of the leg-circumference elastic members 61. That is, since the stretching force for each string of the leg-circumference elastic members 61 can be made smaller, a burden on the skin caused by local close contact with the leg-circumference elastic members 61 can be prevented.

The leg-circumference extension sections 60 in an embodiment of the present disclosure are formed of the exterior sheet 14 of the absorbent main body 10, and include the overlap portions 60b, that overlap with the waist-circumference sections 20, 30. As illustrated in FIG. 5, a portion of the overlap portions 60b is joined to the waist-circumference section 20, 30 with the adhesive region 40. Thus, the overlap portions 60b are likely to be affected by lateral contraction of the waist-circumference sections 20, 30. In particular, when the leg-circumference extension sections 60 are wide in width as in the diaper 1 according to an embodiment of the present disclosure, the overlap portions 60b result in being large accordingly, and thus the leg-circumference extension sections 60 are likely to be affected by the waist-circumference sections 20, 30. This might lead to the leg opening forming portions 60a of the leg-circumference extension sections 60 contracting in the lateral direction, or curling inwards or outwards. For example, if in the processes for manufacturing the diapers 1, the diaper 1 is individually packaged with the leg opening forming portion 60a in a curled and folded state, then a trace of folding would remain in the leg opening forming portion 60a, resulting in the diaper 1 being worn with the leg opening forming portion 60a in a folded state. Accordingly, the leg-circumference extension sections 60 might not be able to closely fit around the wearer's legs through face contact, even though the leg-circumference extension sections 60 are set wide in width.

Thus, in the diaper 1 according to an embodiment of the present disclosure, a plurality of the lateral welded regions 62, having a predetermined lateral length (L1 in FIG. 6), are placed in each of the overlap portions 60b overlapped with the waist-circumference section 20, 30 in the leg-circumference extension section 60.

The stiffness in the lateral direction of the overlap portions 60b is accordingly increased by virtue of the lateral welded regions 62. That is, the lateral welded regions 62 resist lateral contraction of the waist-circumference sections 20, 30, so that the overlap portions 60b are not likely to contract in the lateral direction. As a result, the leg opening forming portions 60a are also suppressed from contracting or curling in the lateral direction, so that the leg opening forming portions 60a are likely to be maintained in a state of having some lateral width (a wide-width state).

This can closely fit the leg opening forming portions 60a around the legs of the wearer through a face having a wide width, thereby suppressing leakage of excrement from around the legs of the wearer. Moreover, in the diaper in the natural state (FIG. 1), since the leg opening forming portions 60a extend in the lateral direction substantially horizontally, the leg opening forming portions 60a closely fit around the legs of the wearer through face contact simply by the wearer's passing their legs through the leg openings LH of the diaper 1. This makes such an action unnecessary as pulling out leg opening forming portions 60a that have curled inwards using fingers, for example, thereby being able to easily wear the diaper 1 appropriately. Further, the wide width leg-circumference extension sections 60 closely fit the wearer, thereby being able to cover the buttocks of the wearer. Thus, there is no need to provide, for example, a cover or the like to cover the buttocks separately from the waist-circumference sections 20, 30, enabling simple configuration of the diaper 1.

Further, in the diaper 1, the stiffness of the overlap portions 60b is increased by placing the lateral welded regions 62 in the overlap portions 60b. This can facilitate manufacturing of the diapers 1 more, as compared with a case in which the stiffness of the overlap portions 60b is increased by respectively providing separate members onto the overlap portions 60b, for example.

Note that the lateral welded regions 62 according to an embodiment of the present disclosure are, as illustrated in FIG. 7, formed such that dot-shaped weld portions 69 (for example, weld portions that are each formed by a protrusion in a protrusion pattern provided on the outer circumferential face of an embossing roller) are formed to be arranged in the lateral direction. Specifically, pairs of rows each having three dots of the weld portions 69 arranged to be inclined with respect to the lateral direction are arranged in rows in the vertical direction without being aligned with one another in the lateral direction. Similarly, the vertical welded regions 66 are also formed such that pairs of rows each having multiple of the dot-shaped weld portions 69 along the vertical direction are arranged in the lateral direction without being aligned with one another in the vertical direction. Accordingly, such welded regions 62, 66 may be obtained by being partially welded, and in this case also, the lateral stiffness of the overlap portions 60b is increased. Note that it is not limited thereto and, for example, the planar shape of a single protrusion provided on the outer circumferential face of an embossing roller may be formed into the same shape as each welded region 62, 66, such that the entire welded region 62, 66 are welded. However, by forming each shape of the weld portions 69 to be small as in an embodiment of the present disclosure, a pressure applied when welding is likely to be constant, thereby achieving stable welding.

The predetermined lateral length of the lateral welded regions 62 may be of any length as long as it is greater than 0 mm, however the welded regions 62 are preferably elongated to some extent. For example, in cases in which the lateral width of the leg-circumference extension sections 60 is 40 mm, the length in the lateral direction of the lateral welded regions 62 is preferably in a range from 7.5 mm to 27.5 mm, and is more preferably about 17.5 mm.

Moreover, the predetermined length in the lateral direction of the lateral welded regions 62 (for example, L1 in FIG. 6) indicates a length in the lateral direction from one end to the other end in the lateral direction of the lateral welded regions 62. Accordingly, the shape of the lateral welded regions 62 may be a shape extending parallel to the lateral direction (not illustrated), and may also be a shape inclined with respect to the lateral direction as in an embodiment of the present disclosure. However, for example, when the axial direction of an embossing roller corresponds to the lateral direction of the lateral welded regions 62 and the lateral welded regions 62 are parallel to the lateral direction, the lateral welded regions 62 are formed all at once. In contrast thereto, when the lateral welded regions 62 are inclined with respect to the lateral direction, each of the lateral welded regions 62 is formed by sequential application of pressure as the embossing roller rotates, thereby achieving stable welding.

Further, the shape of the lateral welded regions 62 is not limited to line shapes in which the dot-shaped weld portions 69 are arranged in the lateral direction as in an embodiment of the present disclosure. The lateral welded regions 62 may be formed, for example, in a rectangular shape, trapezoidal shape, elliptical shape, barrel shape, or the like that are elongated in the lateral direction. Further, the weld portions 69 are not limited to the dot-shaped weld portions 69, and the lateral welded regions 62 may be formed such that weld portions 69 of another shape, such as a square shape, a triangular shape, or the like are placed in the lateral direction. Furthermore, a plurality of the lateral welded regions 62 may be arranged in the lateral direction in each of the overlap portions 60b. The number of the lateral welded regions 62 in each of the overlap portions 60b may be any as long as it is one or more.

In the diaper 1 according to an embodiment of the present disclosure, the leg-circumference extension sections 60 includes the two overlap portions 60b that are each overlapped with either the front waist-circumference section 20 or the back waist-circumference section 30, however, the leg-circumference extension sections 60 may have another configuration as long as a leg-circumference extension section 60 is overlapped with at least one of the front waist-circumference section 20 and the back waist-circumference section 30. Moreover, in the diaper 1 according to an embodiment of the present disclosure, the lateral welded regions 62 are placed in both the overlap portion 60b overlapped with the front waist-circumference section 20 and the overlap portion 60b overlapped with the back waist-circumference section 30, however, lateral welded regions 62 may be placed in only one of these overlap portions 60b. However, the leg opening forming portions 60a are likely to be maintained in a wide-width state when the lateral welded regions 62 are disposed in both of the overlap portions 60b.

In the diaper 1 according to an embodiment of the present disclosure, a plurality of the lateral welded regions 62 are placed also in the leg opening forming portions 60a of the leg-circumference extension sections 60. Thus, the lateral stiffness of the leg opening forming portions 60a themselves is also high, and the leg opening forming portions 60a are not likely to be affected by contraction in the lateral direction of the waist-circumference sections 20, 30. Accordingly, the leg opening forming portions 60a are further likely to be maintained in the wide-width state and the leg opening forming portions 60a closely fit around the legs of the wearer through face contact, so that leakage from around the legs is suppressed more reliably.

As illustrated in FIG. 5, the plurality of lateral welded regions 62 are arranged at constant intervals in the longitudinal direction across the entire longitudinal region of the leg-circumference extension sections 60a, thereby facilitating an adjustment to the intervals in forming the lateral welded regions 62. Accordingly, manufacturing of the diaper 1 is facilitated.

However, the lateral welded regions 62 may not be placed in the leg opening forming portions 60a. In such a case also, the leg opening forming portions 60a are maintained in the wide-width state by virtue of the lateral welded regions 62 in the overlap portions 60b. Further, in this case, since the number of the lateral welded regions 62, which are comparatively hard, is reduced, the burden on the skin can be reduced, which makes the diaper 1 more comfortable to wear.

As illustrated in FIG. 6, the plurality of waist-circumference elastic members 22, 32 are arranged at intervals in the vertical direction in the waist-circumference sections 20, 30, and the plurality of lateral welded regions 62 are arranged at intervals in the vertical direction in the overlap portions 60b. A vertical interval L3 between the plurality of waist-circumference elastic members 22, 32 is smaller than a vertical interval L2 between the plurality of lateral welded regions 62 arranged in the overlap portions 60b (L2>L3).

Accordingly, the number of the waist-circumference elastic members 22, 32 is not too small, which can ensure the fit of the waist-circumference sections 20, 30 to the wearer. That is, it is possible to ensure the fit of the waist-circumference sections 20, 30 to the wearer while suppressing lateral contraction of the overlap portions 60b and leakage from around the legs by virtue of the lateral welded regions 62. Moreover, the number of the lateral welded regions 62 placed in the overlap portions 60b is not too great, which can prevent increase in burden on the skin caused by the comparatively hard lateral welded regions 62. Further, the overlap portions 62 can be prevented from being torn from the lateral welded regions 62 due to the intervals between the lateral welded regions 62 being too small.

However, the configuration is not limited to the above. The vertical interval L2 of the lateral welded regions 62 placed in the overlap portions 60b may be equal to or smaller than the vertical interval L3 of the waist-circumference elastic members 22, 32. In this case, the number of the lateral welded regions 62 is increased, so that lateral contraction of the overlap portions 60b is suppressed more reliably. The above comparison may be made using an interval between the waist-circumference elastic members 22, 32 located at the same vertical position as that of the overlap portions 60b, or using an interval between the waist-circumference elastic members 22, 32 located above the overlap portions 60b. In cases where the intervals between the lateral welded regions 62 and the intervals between the waist-circumference elastic members 22, 32 are not constant, the intervals therebetween may not be constant as long as at least one of the intervals between the waist-circumference elastic members 22, 32 is smaller than at least one of the intervals between the lateral welded regions 62.

The lateral welded regions 62 placed in the overlap portions 60*b* are preferably not superimposed on the waist-circumference elastic members 22, 32 in plan view in the thickness direction of the leg-circumference extension sections 60 (FIG. 6). That is, the lateral welded regions 62 preferably deviate in the vertical direction from the waist-circumference elastic members 22, 32. This prevents contraction in portions of the waist-circumference elastic members 22, 32 that are overlapped with the overlap portions 60*b* from being excessively suppressed by the lateral welded regions 62, so that such portions of the waist-circumference elastic members 22, 32 contract appropriately. Accordingly, it is possible to effectively utilize the waist-circumference elastic members 22, 32 and ensure the fit of the waist-circumference sections 20, 30 to the wearer. However, it is not limited thereto. The vertical positions of a part or all of the plurality of lateral welded regions 62 may coincide with vertical positions of the waist-circumference elastic members 22, 32.

As illustrated in FIG. 6, waist-circumference elastic members 22*a*, 32*a* located above the absorbent body 12 in the vertical direction extend continuously from one side portion to the other side portion in the lateral direction of the waist-circumference section 20, 30. In contrast, waist-circumference elastic members 22*b*, 32*b* located at the same vertical position as the absorbent body 12 each include a portion from one side portion in the lateral direction of the waist-circumference section 20, 30 to one side portion in the lateral direction of the absorbent body 12, and a portion from the other side portion in the lateral direction of the absorbent body 12 to the other side portion in the lateral direction of the waist-circumference section 20, 30. That is, the waist-circumference elastic members 22*b*, 32*b* each include a discontinuous portion in a position superimposed on the absorbent body 12 in the thickness direction of the waist-circumference section 20, 30 (for example, point a-point b in FIG. 6).

Thus, the absorbent body 12 is not likely to be affected by lateral contraction of the waist-circumference elastic members 22, 32, thereby being able to suppress the absorbent body 12 from be twisted. This can cause the absorbent body 12 to closely fit the wearer such that excrement is properly absorbed by the absorbent body 12, thereby suppressing leakage from around the legs. Since the absorbent body 12 is suppressed from being twisted, the leg opening forming portions 60*a* can be extended substantially horizontally to the lateral direction. This can closely fit the leg opening forming portions 60*a* around the wearer's legs through face contact, thereby suppressing leakage from around the legs.

As illustrated in FIG. 3, the lateral welded regions 62 placed in the overlap portions 60*b* and the lateral welded regions 62 placed in the leg opening forming portions 60*a* both include the first lateral welded regions 63 and the second lateral welded regions 64. The second lateral welded regions 64 are positioned on the non-skin side in the thickness direction of the extension sections 60 with respect to the first lateral welded regions 63. Accordingly, the lateral stiffness of the overlap portions 60*b* and the leg opening forming portions 60*a* is further increased. The exterior sheet 14 is folded into a quadruple layer to superimpose the first lateral welded regions 63 and the second lateral welded regions 64 on each other. As such, the lateral stiffness of the overlap portions 60*b* and the leg opening forming portions 60*a* is increased also with increase in the number of stacked layers of the exterior sheet 14. Accordingly, the overlap portions 60*b* are further less likely to be affected by contraction of the waist-circumference sections 20, 30, and the leg opening forming portions 60*a* are more likely to be maintained in a wide-width state. This can closely fit the leg opening forming portions 60*a* around the legs of the wearer through face contact, and suppress leakage from around the legs more reliably.

In other words, with the first lateral welded regions 63 and the second lateral welded regions 64 being superimposed on each other, the stiffness of the overlap portions 60*b* and the stiffness of the leg opening forming portions 60*a* can be ensured even when the stiffness is lowered by reducing the welding strength per lateral welded region 62. Accordingly, the lateral welded regions 62 can be comparatively softened, which makes the diaper 1 more comfortable to wear. Further, it is possible to prevent the lateral welded regions 62 from becoming too thin or into holes, which results from trying to increase the welding strength so as to increase the stiffness of the lateral welded regions 62.

However, it is not limited thereto. The plurality of lateral welded regions 62 may not be superimposed on each other in the thickness direction in the overlap portions 60*b* and the leg opening forming portions 60*a*, as long as the exterior sheet 14 is folded into a double layer and the double layer is welded to form the lateral welded regions 62. Alternatively, three of more of the lateral welded regions 62 may be superimposed on each other in the thickness direction.

The overlap portions 60*b* each include a non-joined region 41 (the regions 41 surrounded by bold lines in FIG. 5) where the overlap portion 60*b* and the waist-circumference section 20, 30 are not joined together in a position corresponding to the lower end portion in the vertical direction of the waist-circumference section 20, 30. Lateral welded region 62*a* is placed in the non-joined region 41.

In the overlap portions 60*b*, the non-joined regions 41 are less likely to be affected by lateral contraction of the waist-circumference sections 20, 30 than the joined regions 40 where the overlap portions 60*b* are joined to the waist-circumference sections 20, 30 (diagonally hatched regions in FIG. 5). Accordingly, by providing the non-joined region 41 in each boundary portion between the overlap portion 60*b* and the leg opening forming portion 60*a*, the boundary portion is likely to be maintained in the wide-width state. Moreover, by placing the lateral welded regions 62*a* in the boundary portion (the non-joined regions 41), the boundary portion is more likely to be maintained in a wide-width state. As a result, the leg opening forming portion 60*a* is also likely to be maintained in the wide-width state. In other words, the lateral contraction force from the waist-circumference sections 20, 30 is blocked by the lateral welded regions 62 in the non-joined regions 41, so that the lateral contraction force is less likely to be transferred to the leg opening forming portions 60*a*. Consequently, the leg opening forming portions 60*a* are likely to be maintained in the wide-width state. Thus, the leg opening forming portions 60*a* can closely fit around the legs of the wearer through face contact, thereby suppressing leakage from around the legs.

In the diaper 1, in addition to the joined regions 40 described above, joined regions 42, 43, 44 as illustrated in FIG. 3 are also provided, where the adhesive agent is applied. Specifically, the first sheet portion 14*a* and the second sheet portion 14*b* of the exterior sheet 14 forming the leak prevention wall sections 50 are joined in the joined regions 42. The non-skin-side face of the absorbent body 12 wrapped in the top sheet 11, and the back sheet 13 are also joined in the joined region 43. The back sheet 13 and the exterior sheet 14 are also joined in the joined region 44.

Whereas, in laterally outer portions 60*c* of the leg-circumference extension sections 60 illustrated in FIG. 3 (more specifically at the portions 60c further laterally outside of the side joined portions 53 in the leak prevention wall sections 50), the first sheet portion 14a and the second sheet portion 14b of the exterior sheet 14 are not joined together with adhesive over the entire longitudinal region thereof. Similarly, the third sheet portion 14c and the fourth sheet portion 14d of the exterior sheet 14 are not joined together with adhesive over the entire longitudinal region thereof. That is, the first sheet portion 14a and the second sheet portion 14b of the exterior sheet 14 are not joined together at portions each between the first lateral welded regions 63 arranged along the longitudinal direction (for example, the portions 65 in FIG. 5), so that gaps are each created therebetween, resulting in high cushioning properties being provided. Similarly, the third sheet portion 14c and the fourth sheet portion 14d of the exterior sheet 14 are not joined together at portions each between the second lateral welded regions 64 arranged along the longitudinal direction, so that gaps are each created therebetween, resulting in high cushioning properties being provided. Accordingly, by enhancing cushioning properties of the leg-circumference extension sections 60 as such, the diaper 1 becomes more comfortable to wear.

Further, in the diaper 1 according to an embodiment of the present disclosure, since the first lateral welded regions 63 and the second lateral welded regions 64 are superimposed on each other in the thickness direction, the first sheet portion 14a and the second sheet portion 14b having high cushioning properties are further superimposed on the third sheet portion 14c and the fourth sheet portion 14d having high cushioning properties. Accordingly, the cushioning properties in the leg-circumference extension sections 60 are further enhanced.

The first vertical welded regions 67 and the second vertical welded regions 68 are also provided in the leg-circumference extension sections 60 according to an embodiment of the present disclosure. Thus, even though the first sheet portion 14a and the second sheet portion 14b are not joined together between the first lateral welded regions 63, the first sheet portion 14a and the second sheet portion 14b are firmly and closely joined together by the first vertical welded regions 67. Similarly, the third sheet portion 14c and the fourth sheet portion 14d are also firmly and closely joined together by the second vertical welded regions 68. Thus, the first sheet portion 14a and the second sheet portion 14b are not likely to separate from each other, and the third sheet portion 14c and the fourth sheet portion 14d are not likely to separate from each other, for example, even when the sheet portions are sandwiched between the wearer's legs. Accordingly, the leg opening forming portions 60a are maintained in the wide-width state. However, the first vertical welded regions 67 and the second vertical welded regions 68 may not be provided.

The lateral welded regions 62 according to an embodiment of the present disclosure are inclined with respect to the lateral direction. Accordingly, the vertical length of the non-joined portions between the first sheet portion 14a and the second sheet portion 14b when the lateral regions 62 are inclined is smaller than the vertical length of the non-joined portions, for example, when the lateral regions 62 are parallel to the lateral direction. Also, the vertical length of the non-joined portions between the third sheet portion 14c and the fourth sheet portion 14d when the lateral regions 62 are inclined is also smaller than the vertical length when the lateral regions 62 are parallel thereto. Thus, the first sheet portion 14a and the second sheet portion 14b are not likely to separate, and the third sheet portion 14c and the fourth sheet portion 14d are not likely to separate, so that the leg opening forming portions 60a are maintained in the wide-width state.

In the overlap portions 60b in the laterally outer portions 60c of the leg-circumference extension sections 60, the second sheet portion 14b of the exterior sheet 14 and the back sheet 13, and the back sheet 13 and the third sheet portion 14c of the exterior sheet 14, may not be joined together with adhesive. In particular, since the back sheet 13 and the third sheet portion 14c are not joined together, end portions that are not fixed in a stretched state of the leg-circumference elastic members 61 are able to contract. This can prevent the leg-circumference elastic members 61 from being exposed from the two longitudinal end portions of the leg-circumference extension sections 60. The third sheet portion 14c and the fourth sheet portion 14d of the exterior sheet 14 are joined to the waist-circumference sections 20, 30 through the adhesive regions 40 and the lateral welded regions 62. However, the first sheet portion 14a and the second sheet portion 14b of the exterior sheet 14 are away from the waist-circumference sections 20, 30, and thus are not likely to be affected by lateral contraction of the waist-circumference sections 20, 30. Accordingly, the leg opening forming portions 60a are likely to be maintained in the wide-width state. Even without joining the above-described portions together, the end portions on the two longitudinal ends of the leg-circumference extension sections 60 can be suppressed from being opened since the lateral welded regions 62 are placed in the overlap portions 60b.

In the leg opening forming portions 60a of the laterally outer portions 60c in the leg-circumference extension sections 60, the second sheet portion 14b of the exterior sheet 14 and the back sheet 13, and the back sheet 13 and the third sheet portion 14c of the exterior sheet 14 are preferably joined together with adhesive. With such a configuration, the four layers 14a to 14d of the exterior sheet 14 are prevented from separating from each other when being sandwiched between the wearer' s legs. Thus, the leg opening forming portions 60a are maintained in the wide-width state.

Further, as illustrated in FIG. 6, the lateral welded regions 62 are placed inside of laterally outer ends 60d of the leg-circumference extension sections 60 in the leg opening forming portions 60a of the leg-circumference extension sections 60. That is, the lateral welded regions 62 are absent in end portions on the laterally outer side in the leg opening forming portions 60a, so that these end portions are soft and accordingly comfortable to the skin of the wearer's legs contacting the end portions, which makes the diaper 1 more comfortable to wear. Further, the sandwiching force of the wearer's legs is absorbed. Thus, the leg opening forming portions 60a are likely to be maintained in the wide-width state, which closely fit the leg opening forming portions 60a around the legs of the wearer through face contact, thereby suppressing leakage from around the legs.

Further, as illustrated in FIG. 3, in the absorbent main body 10, the back sheet 13 is disposed between the absorbent body 12 wrapped in the top sheet 11 and the exterior sheet 14 as well as between folded portions of the exterior sheet 14. As illustrated in FIG. 2, laterally outer ends 13a of the back sheet 13 are also disposed inside of the laterally outer ends 60d of the leg-circumference extension sections 60, respectively. Accordingly, the back sheet 13 is absent in the end portions on the laterally outer side in the leg opening forming portions 60a, so that these end portions are soft and thus comfortable to the skin of the wearer's legs contacting the end portions, which makes the diaper 1 more comfortable to wear. Further, the sandwiching force of the wearer's legs is absorbed, and thus the leg opening forming portions 60a are maintained in the wide-width state.

As illustrated in FIG. 2 and FIG. 3, in each of the leg opening forming portions 60a, four leg-circumference elastic members 61a to 61d are placed side by side in the lateral direction. Two leg-circumference elastic members 61b, 61c positioned in the center thereof intersect with the lateral welded regions 62 placed in the leg opening forming portions 60a. The portions where the lateral welded regions 62 are placed in the leg opening forming portions 60a have high stiffness, and thus are likely to be maintained in a planar shape. The portions where the lateral welded regions 62 are placed in the leg opening forming portion 60a are integrally raised to the wearer's side by virtue of contraction of the leg-circumference elastic members 61b, 61c. Thus, as illustrated in FIG. 7, such portions where the lateral welded regions 62 are placed in the leg opening forming portions 60a can closely fit around the legs of the wearer through face contact, thereby suppressing leakage from around the legs.

The leg-circumference elastic member 61a that is positioned on the innermost side in the lateral direction among the four leg-circumference elastic members 61a to 61d is placed at a position between the absorbent body 12 and the lateral welded regions 62 in the lateral direction. Thus, as illustrated in FIG. 7, portions laterally outside of the leg-circumference elastic members 61a are raised to the wearer's side by virtue of contraction of the leg-circumference elastic members 61a, thereby ensuring an upright height. This can make it possible to closely fit the leg opening forming portions 60a around the legs of the wearer.

The leg-circumference elastic member 61d that is positioned on the outermost side in the lateral direction among the four leg-circumference elastic members 61a to 61d is placed at the position of the laterally outer end 60d of each of the leg opening forming portions 60a. Accordingly, the leg opening forming portions 60a are capable of securely fitting the wearer up to the position of the laterally outer ends 60d by virtue of contraction of the leg-circumference elastic members 61d. In particular, even in a case in which the lateral welded regions 62 do not reach the laterally outer ends 60d in the leg opening forming portions 60a, the leg opening forming portions 60a can closely fit the wearer up to the position of the laterally outer ends 60d.

In the diaper 1 according to an embodiment of the present disclosure, the leg-circumference extension sections 60 (the leg opening forming portions 60a) are formed using the exterior sheet 14, which extends laterally outward from the position on the non-skin-side surface side of the absorbent body 12 and is continuous in the lateral direction. The position on the non-skin-side surface side of the absorbent body 12 refers to the position on the non-skin side in the thickness direction with respect to the absorbent body 12 as well as the position overlapping with the absorbent body 12 in the lateral direction.

Assuming here that the exterior sheet 14 has about the same lateral width as that of the absorbent body 12, and the leg opening forming portions 60a are formed using side sheets that are members separate from the exterior sheet 14 and that extend laterally outward from the exterior sheet 14, seams between the exterior sheet 14 and the side sheets would be exposed to the non-skin-side face in the vicinity of the leg opening forming portions 60a. Further, assuming that, for example, leg opening forming portions 60a are formed not by folding back the two lateral side portions of the exterior sheet 14 to overlap, but by attaching side sheets that are members separate from the exterior sheet 14 onto the skin-side face of the exterior sheet 14, seams between the exterior sheet 14 and the side sheets would be exposed to the laterally outer ends of the leg opening forming portions 60a. With such a configuration, excrement would seep out from the seams between sheets.

Thus, by forming the leg opening forming portions 60a using the exterior sheet 14 as in the diaper 1 according to an embodiment of the present disclosure, it is possible to prevent the seams between sheets from being exposed to the non-skin-side surface in the vicinity of the leg opening forming portions 60a. Further, in the diaper 1 according to an embodiment of the present disclosure, the lateral welded regions 62 are placed in the leg-circumference extension sections 60 and the side portions of the exterior sheet 14 are folded over to overlap. Accordingly, seams between sheets are not exposed to the laterally outer ends 60d of the leg-circumference extension sections 60. Thus, it is possible to prevent excrement from seeping out from seams between sheets, thereby being able to further suppress leakage from around the legs.

Furthermore, in the diaper 1 according to an embodiment of the present disclosure, the leak prevention wall sections 50 are also formed using the exterior sheet 14. In such a case, there are no seam in the sheet in each boundary between the leak prevention wall section 50 and the leg-circumference extension section 60, thereby being able to further suppress leakage from around the legs. For example, it is possible to suppress excrement blocked by the leak prevention wall sections 50 from seeping out from each boundary between the leak prevention wall section 50 and the leg-circumference extension section 60 to soil the legs of the wearer.

The exterior sheet 14 also extends laterally outward from position on the non-skin-side surface side of the absorbent body 12. That is, the pair of leg-circumference extension sections 60 and the pair of leak prevention wall sections 50 are formed using the shared exterior sheet 14. Accordingly, no seam in the exterior sheet 14 exposed to the non-skin-side surface of the absorbent main body 10, thereby suppressing leakage from a seam in the sheet. Further, the pair of leg-circumference extension sections 60 is integrally raised together when the diaper 1 is worn. Accordingly, the pair of leg-circumference extension sections 60 can closely fit around the legs of the wearer in a balanced manner, thereby suppressing leakage from around the legs.

The number of materials can be reduced by forming the leg-circumference extension section 60 and the leak prevention wall section 50 using the exterior sheet 14 and by forming the pair of leg-circumference extension sections 60 and the pair of leak prevention wall sections 50 using the shared exterior sheet 14, as described above. Accordingly, cost reduction can be achieved. However, it is not limited to the above, and the leg-circumference extension section 60 may be formed using a sheet separate from the exterior sheet 14 (e.g. side sheets added to the exterior sheet 14 or the like).

Modified Examples

Figure 9A:
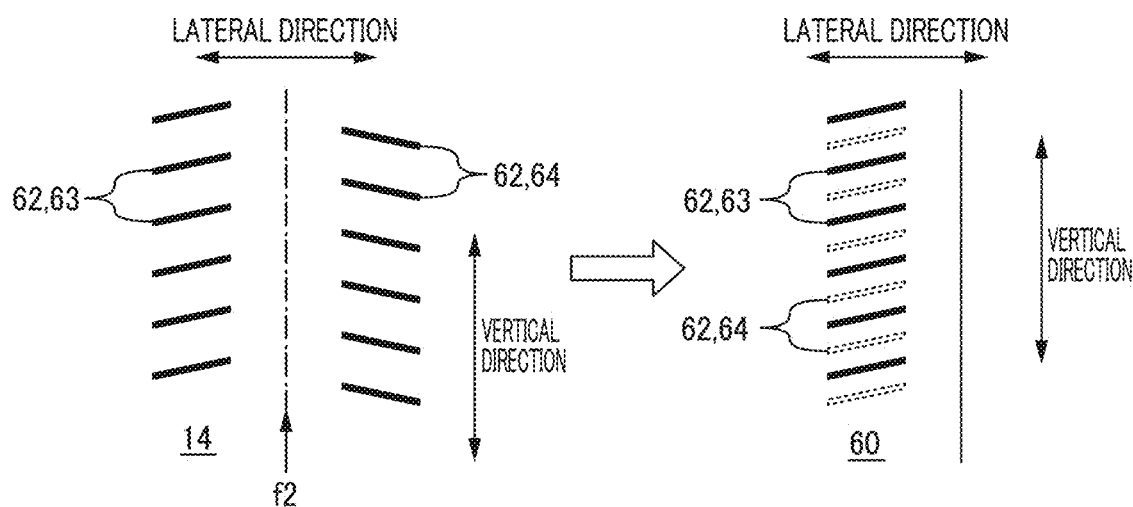
FIG. 9A to FIG. 9C are diagrams to explain modified examples of the lateral welded regions 62.
Figure 9B:
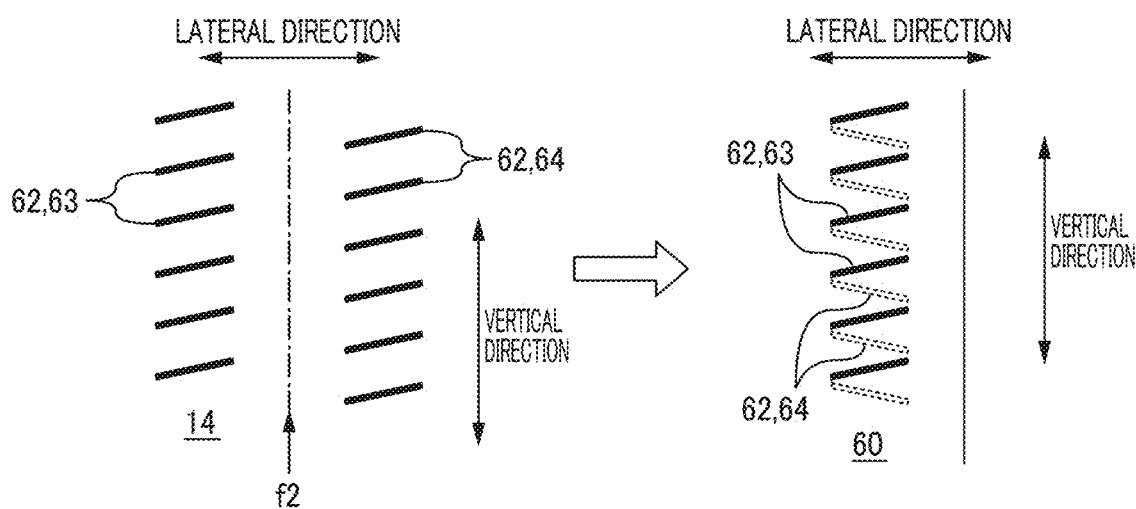
Figure 9C:
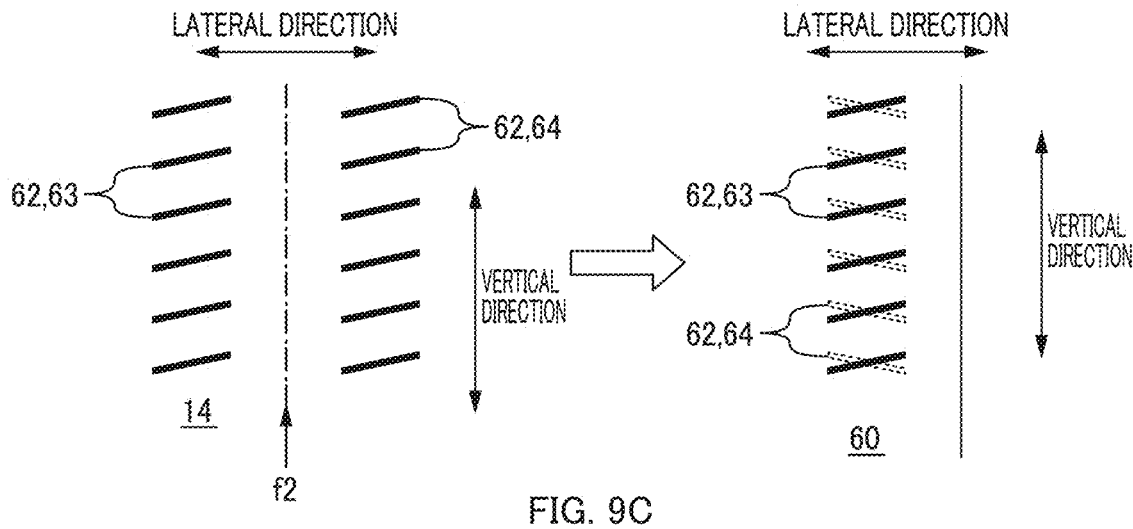

FIG. 9A to FIG. 9C are diagrams for explaining modified examples of the lateral welded regions 62. Diagrams on the left side of FIG. 9A to FIG. 9C illustrate a state in which the first lateral welded regions 63 and the second lateral welded regions 64 have been formed in the exterior sheet 14 during manufacture of the diaper 1. The diagrams on the right side illustrate positional relationships between the first lateral welded regions 63 and the second lateral welded regions 64 in the leg-circumference extension sections 60.

In an embodiment described above, the first lateral welded regions 63 and the second lateral welded regions 64 are formed symmetrically with respect to the fold position f2 of the exterior sheet 14, as illustrated in FIG. 4, that is, their inclination directions are symmetrical to each other and vertical positions match each other. Accordingly, in each of the overlap portions 60b and the leg opening forming portions 60a, the first lateral welded regions 63 and the second lateral welded regions 64 are placed so as to be superimposed on each other in the thickness direction. However, it is not limited thereto. Some or all of the first lateral welded regions 63 and the second lateral welded regions 64 may not be superimposed on each other in plan view in the thickness direction. That is, in each of the overlap portions 60b and the leg opening forming portions 60a, the positions in a flat plane (the positions in the lateral direction and the vertical direction) of the first lateral welded regions 63 may deviate from the positions in a flat plane of the second lateral welded regions 64.

For example, as illustrated on the left side in FIG. 9A, the first lateral welded regions 63 and the second lateral welded regions 64 may be formed such that their inclination directions are symmetrical with respect to the fold position f2 and their positions deviate from each other in the vertical direction. In such a case, as illustrated on the right side of FIG. 9A, the first lateral welded regions 63 and the second lateral welded regions 64 that are inclined in the same direction as each other are arranged alternately in the vertical direction in plan view of the leg-circumference extension sections 60.

For example, as illustrated on the left side of FIG. 9B, the first lateral welded regions 63 and the second lateral welded regions 64 may be formed such that their inclination directions thereof are the same with respect to the fold position f2 and their positions deviate from each other in the vertical direction. In such a case, as illustrated on the right side of FIG. 9B, the first lateral welded regions 63 and the second lateral welded regions 64 that are inclined in directions reverse to each other are arranged alternately in the vertical direction in plan view of the leg-circumference extension sections 60.

For example, as illustrated on the left side of FIG. 9C, the first lateral welded regions 63 and the second lateral welded regions 64 may be formed such that their inclination directions are the same with respect to the fold position f2 and their positions are the same in the vertical direction. In such a case, as illustrated on the right side of FIG. 9C, the first lateral welded regions 63 and the second lateral welded regions 64 that are inclined in directions reverse to each other are arranged so as to intersect each other in plan view of the leg-circumference extension sections 60.

As illustrated in FIG. 9A and FIG. 9B, the first lateral welded regions 63 and the second lateral welded regions 64 may completely deviate from each other, or alternatively, as illustrated in FIG. 9C, a portion of each first lateral welded region 63 and a portion of each second lateral welded region 64 may be superimposed on each other, while the remaining portions thereof may deviate from each other. Accordingly, since the first lateral welded regions 63 and the second lateral welded regions 64 deviate from each other in plan view in the thickness direction, the lateral welded regions 62 are present in a wider range of a flat plane in the overlap portions 60b and the leg opening forming portions 60a, thereby enhancing lateral stiffness of the overlap portions 60b and the leg opening forming portions 60a. Thus, the overlap portions 60b are less likely to be affected by lateral contraction of the waist-circumference sections 20, 30, so that the leg opening forming portions 60a are likely to be maintained in the wide-width state, thereby suppressing leakage from around the legs.

As illustrated in FIG. 9A and FIG. 9B, in a case where the first lateral welded regions 63 and the second lateral welded regions 64 completely deviate from each other, the lateral welded regions 62 are formed by sequentially applying pressure with rotation of an embossing roller, for example, when welding is performed. This results in stable welding. Further, although not illustrated, some of the plurality of first lateral welded regions 63 may be superimposed on the second lateral welded regions 64, and the remaining first lateral welded regions 63 may not be superimposed on the second lateral welded regions 64. Further, the size and the shape in plan view of the first lateral welded regions 63 may also be different from those of the second lateral welded regions 64, and the size and the shape in plan view may be different among the first lateral welded regions 63 and/or among the second lateral welded regions 64. Further, the first lateral welded regions 63 and the second lateral welded regions 64 may also be different in arrangement between in the overlap portions 60b and in the leg opening forming portions 60a. Further, the number of the first lateral welded regions 63 may be different from the number of the second lateral welded regions 64. For example, the number of the second lateral welded regions 64 on the non-skin side is made greater than the number of the first lateral welded regions 63 on the skin side, thereby being able to enhance the comfort to the skin while enhancing the lateral stiffness of the leg-circumference extension sections 60.

The above embodiments of the present disclosure are simply to facilitate understanding of the present disclosure and are not in any way to be construed as limiting the present disclosure. The present disclosure may variously be changed or altered without departing from its gist and encompass equivalents thereof.

For example, such a diaper (so-called a two piece type of diaper) may be employed that is integrated by coupling a front waist-circumference section 20 and a back waist-circumference section 30 together using an exterior sheet 14.

REFERENCE SIGNS LIST

1: diaper (pull-on absorbent article);
10: absorbent main body; 11: top sheet;
12: absorbent body; 121: absorbent core; 122: core-wrapping sheet;
13: back sheet; 14: exterior sheet;
20: front waist-circumference section (waist-circumference section); 21 sheet; 21 sheet
22: waist-circumference elastic member (elastic member stretchable in the lateral direction);
30: back waist-circumference section (waist-circumference section); 31 sheet; 31 sheet;
32 waist-circumference elastic member (elastic member stretchable in the lateral direction);
40: adhesive region; 41: non-joined region; 42 to 44 joined region;
50: leak prevention wall section; 51: elastic member;
52: end joined portion; 53: side joined portion;
60: leg-circumference extension sections (extension section);
60a: leg opening forming portion; 60b: overlap portion;
61: leg-circumference elastic members (elastic member stretchable in the vertical direction);
62: lateral welded regions (welded region);
63: first lateral welded region (first welded region)
64: second lateral welded regions (second welded region)
66: vertical welded region; 67: first vertical welded region;
68: second vertical welded region; 69: weld portion;
LH: leg opening; and BH: waist opening.

The invention claimed is:

1. A pull-on absorbent article having a vertical direction and a lateral direction, the pull-on absorbent article comprising:
    an absorbent main body including an absorbent body, the absorbent main body having a longitudinal direction that conforms to the vertical direction; and
    waist-circumference sections in a pair respectively located on one end side and another end side in the longitudinal direction of the absorbent main body, the waist-circumference sections including a plurality of elastic members stretchable in the lateral direction and placed at a first interval in the vertical direction in the waist-circumference sections,
    the absorbent main body including extension sections in a pair respectively extending outward on two lateral sides of the absorbent body, the extension sections each having an elastic member stretchable in the vertical direction and placed therein,
    the extension sections each forming a leg opening and including an overlap portion that overlaps in the vertical direction with at least one of the waist-circumference sections in a pair,
    the extension sections and the at least one of the waist-circumference sections being joined together in at least a part of the overlap portion,
    the overlap portion, in the extension sections, having a welded region placed therein, the welded region having a predetermined length in the lateral direction,
    wherein
    the welded region includes a plurality of welded regions placed at a second interval in the vertical direction in the overlap portion of each of the extension sections, and
    the first interval in the vertical direction between the plurality of elastic members placed in the waist-circumference sections is smaller than the second interval in the vertical direction between the plurality of welded regions.

2. The pull-on absorbent article according to claim 1, wherein
    the overlap portion includes a non-joined region at a position corresponding to a lower end portion in the vertical direction of the at least one of the waist-circumference sections, the non-joined region being a region where the extension sections and the at least one of the waist-circumference sections are not joined together, and
    the plurality of welded regions is placed in the non-joined region.

3. The pull-on absorbent article according to claim 1, wherein
    the plurality of welded regions and the plurality of elastic members that is placed in the waist-circumference sections are not superimposed on each other in a plan view in a thickness direction of the extension sections.

4. A pull-on absorbent article having a vertical direction and a lateral direction, the pull-on absorbent article comprising:
    an absorbent main body including an absorbent body, the absorbent main body having a longitudinal direction that conforms to the vertical direction; and
    waist-circumference sections in a pair respectively located on one end side and another end side in the longitudinal direction of the absorbent main body, the waist-circumference sections including an elastic member stretchable in the lateral direction,
    the absorbent main body including extension sections in a pair respectively extending outward on two lateral sides of the absorbent body, the extension sections each having an elastic member stretchable in the vertical direction and placed therein,
    the extension sections each forming a leg opening and including an overlap portion that overlaps in the vertical direction with at least one of the waist-circumference sections in a pair,
    the extension sections and the at least one of the waist-circumference sections being joined together in at least a part of the overlap portion,
    the overlap portion, in the extension sections, having a welded region placed therein, the welded region having a predetermined length in the lateral direction, wherein
    the welded region includes a first welded region and a second welded region, the second welded region being positioned on a non-skin side in a thickness direction of the extension sections with respect to the first welded region.

5. The pull-on absorbent article according to claim 4, wherein
    at least a portion of the first welded region and at least a portion of the second welded region are not superimposed on each other in a plan view in the thickness direction.

6. The pull-on absorbent article according to claim 1, wherein
    the plurality of elastic members placed in the waist-circumference sections includes a discontinuous portion in a portion superimposed on the absorbent body in a thickness direction of the waist-circumference sections.

* * * * *